(12) United States Patent
Hurley et al.

(10) Patent No.: US 10,578,569 B2
(45) Date of Patent: Mar. 3, 2020

(54) APPARATUS FOR DETERMINING A THERMAL CONDUCTIVITY AND A THERMAL DIFFUSIVITY OF A MATERIAL, AND RELATED METHODS

(71) Applicant: BATTELLE ENERGY ALLIANCE, LLC, Idaho Falls, ID (US)

(72) Inventors: David H. Hurley, Idaho Falls, ID (US); Robert S. Schley, Rigby, ID (US); Marat Khafizov, Columbus, OH (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 445 days.

(21) Appl. No.: 15/345,330

(22) Filed: Nov. 7, 2016

(65) Prior Publication Data
US 2018/0128759 A1     May 10, 2018

(51) Int. Cl.
*G01N 25/18*     (2006.01)

(52) U.S. Cl.
CPC .................... *G01N 25/18* (2013.01)

(58) Field of Classification Search
CPC ...................................................... G01N 25/18
USPC ............................................................ 374/44
See application file for complete search history.

(56) References Cited

U.S. PATENT DOCUMENTS

| 5,042,952 A | 8/1991 | Opsal et al. |
| 5,344,236 A | 9/1994 | Fishman |
| 5,586,824 A | 12/1996 | Barkyoumb et al. |
| 5,667,300 A | 9/1997 | Mandelis et al. |
| 6,054,868 A | 4/2000 | Borden et al. |
| 6,595,685 B2 | 7/2003 | Baba et al. |

(Continued)

FOREIGN PATENT DOCUMENTS

| EP | 2840385 A1 | 2/2015 |
| WO | 2015027210 A1 | 2/2015 |

OTHER PUBLICATIONS

Fretigny, et al., "Analytical inversion of photothermal measurements: Independent determination of the thermal conductivity and diffusivity of a conductive layer deposited on an insulating substrate", Journal of Applied Physics 102, 116104 (Dec. 2007), pp. 116104-1-116104-3.

(Continued)

*Primary Examiner* — Lisa M Caputo
*Assistant Examiner* — Janice M Soto
(74) *Attorney, Agent, or Firm* — TraskBritt

(57) ABSTRACT

A method of determining a thermal conductivity and a thermal diffusivity of a material comprises exposing a specimen comprising a substrate of a material and a metallic film over the substrate to an amplitude modulated pump laser beam comprising electromagnetic radiation having a first wavelength and a first modulation frequency to form a pump spot on the metallic film. The specimen is exposed to a probe laser beam comprising electromagnetic radiation having a second wavelength to form a probe spot on the metallic film. A phase shift between the pump laser beam and a reflected probe laser beam is measured while scanning the pump spot relative to the probe spot. A modulation frequency of the pump laser beam is changed to a second modulation frequency and the pump spot is scanned relative to the probe spot while detecting the phase shift. A phase profile of the material is measured and a continuum-based model is fit to the phase profile. Related microscopes and related methods are also disclosed.

23 Claims, 3 Drawing Sheets

(56) References Cited

U.S. PATENT DOCUMENTS 6,906,801 B2  6/2005 Borden et al.
7,364,354 B2  4/2008 Lakestani et al.
2009/0274191 A1  11/2009 Hache et al.

OTHER PUBLICATIONS

Gronbeck et al., "Harmonic heat flow in anisotropic thin films", Journal of Applied Physics 78, (11), (Dec. 1995), pp. 6408-6413.
Hartmann et al., "Measuring local thermal conductivity in polycrystalline diamond with a high resolution photothermal microscope", Journal of Applied Physics 81, 2966 (Apr. 1997), pp. 2966-2972.
Hua et al., "Spatially localized measurement of thermal conductivity using a hybrid photothermal technique", Journal of Applied Physics, 111, 103505 (May 2012), pp. 103505-1-103505-7.
Hua et al., "The study of frequency-scan photothermal reflectance technique for thermal diffusivity measurement", Review of Scientific Instruments, 86, 054901, (May 2015), pp. 054901-1-054901-6.
Hurley et al., "Measurement of the Kapitza resistance across a bicrystal interface", Journal of Applied Physics 109, 083504 (Apr. 2011), pp. 08304-1-08304-5.
Hurley et al., "Local measurement of thermal conductivity and diffusivity", Review of Scientific Instruments 86, 12390 (Dec. 2015).
Jackson et al., "Photothermal deflection spectroscopy and detection", Applied Optics, vol. 20, No. 8, (Apr. 1981), pp. 1333-1344.
Koh et al., "Comparison of the 3 w method and time-domain thermoreflectance for measurements of the cross-plane thermal conductivity of epitaxial semiconductors", Journal of Applied Physics 105, 054303 (Mar. 2009), pp. 054303-1-054303-7.
Maznev et al., "Thermal wave propagation in thin films on substrates", Journal of Applied Physics, 78, (9), (Nov. 1995), pp. 5266-5269.
Opsal et al., "Thermal-wave detection and thin-film thickness measurements with laser beam deflection", Applied Optics, vol. 22, No. 20, (Oct. 1983), pp. 3169-3176.
Paddock et al., "Transient thermoreflectance from thin metal films", Journal of Applied Physics, 60, (1), (Jul. 1986), pp. 285-290.
Reichling et al., "Harmonic heat flow in isotropic layered systems and its use for thin film thermal conductivity measurements", Journal of Applied Physics 75, (4) (Feb. 1994), pp. 1914-1922.
Ronchi et al., "Effect of burn-up on the thermal conductivity of uranium dioxide up to 100.000 MWd t-1", Journal of Nuclear Materials 327 (Jan. 2004), pp. 58-76.
Rondinella et al., "The high burn-up structure in nuclear fuel", materialstoday, vol. 13, No. 12, (Dec. 2010), pp. 24-32.
Schmidt et al., "Pulse accumulation, radial heat conduction, and anisotropic thermal conductivity in pump-probe transient thermoreflectance", Review of Scientific Instruments, 79, 114902 (Nov. 2008), pp. 114902-1-114902-9.
Stoner et al., "Kapitza conductance and heat flow between solids at temperatures from 50 to 300K", Physical Review B, vol. 48, No. 22, (Dec. 1993), pp. 16 373-16 387.

APPARATUS FOR DETERMINING A THERMAL CONDUCTIVITY AND A THERMAL DIFFUSIVITY OF A MATERIAL, AND RELATED METHODS

STATEMENT REGARDING FEDERALLY SPONSORED RESEARCH OR DEVELOPMENT

This invention was made with government support under Contract Number DE-AC07-05-ID14517 awarded by the United States Department of Energy. The government has certain rights in the invention.

FIELD

Embodiments of the disclosure relate generally to an apparatus, which may be characterized as a microscope, for measuring a thermal conductivity and a thermal diffusivity of a material, and to related methods. More particularly, embodiments of the disclosure relate to a microscope configured to measure one or both of a thermal conductivity and a thermal diffusivity by exposing a material to a pump laser beam, measuring a phase offset between a probe laser beam reflected from a specimen comprising the material and the pump laser beam, and fitting the measured phase offset to a continuum-based model to determine the thermal conductivity and the thermal diffusivity of the material, and to related methods.

BACKGROUND

Methods of determining a thermal conductivity and a thermal diffusivity of a material include direct current methods, laser flash analysis, or other methods. Direct current methods may include disposing a sample of an unknown thermal conductivity between a heat source and a heat sink, contacting the sample with a standard material (e.g., a so-called "puck"), and inputting a known amount of heat into the sample with the heat source. The thermal conductivity of the sample is proportional to the power input into the sample, the temperature difference between two thermocouples placed across the sample, and the ratio of the length between the thermocouples to the cross-sectional area of the sample $$\left(k = \frac{P}{\Delta T}\left(\frac{L}{A}\right)\right),$$

wherein k is the thermal conductivity, P is the power input into the system, L is the length between the thermocouples, and A is the cross-sectional area of the sample through which the heat flows. However, an accurate measurement of the thermal conductivity requires adequately flowing heat through the sample. Accordingly, the sample must be physically coupled to the heat source and the heat sink. Improperly coupling the sample to the heat source and the heat sink may introduce undesired uncertainty in the measured thermal conductivity of the sample. In addition, it may be difficult to obtain accurate thermal conductivity measurements of thin film samples since coupling methods may damage such samples. Further, as the size of the sample decreases, the accuracy of the temperature measurements to determine the difference in temperatures between the thermocouples must increase.

Laser flash analysis, on the other hand, includes a long pulse laser and an infrared detector. The long pulse laser heats a sample and the infrared detector measures the temperature on the back side of the sample by measuring the black body radiation of the sample. Thus, laser flash analysis requires access to both sides of a sample. Laser flash analysis requires a separate measurement of the specific heat of the sample to determine the thermal conductivity thereof. Use of a laser flash analysis machine requires a particular sample size (e.g., diameter and thickness), depending on the conductivity range of the sample. In addition, smaller samples may require optical focusing of the long pulse laser used to heat the sample. Furthermore, laser flash methods often assume that the sample exhibits only one-dimensional heat flow (through the thickness of the sample). As such, the sample must meet particular thickness and diameter requirements for accurate measurement of thermal conductivity.

Thermal conductivity is an important property of many materials, for various applications. For example, in nuclear fuel systems, the thermal conductivity of nuclear fuel is related to energy conversion efficiency as well as to reactor safety. However, over the lifetime of nuclear fuel, the thermal conductivity thereof may degrade due to changes in material microstructure caused by neutron irradiation. In addition, the microstructure of the nuclear fuel may change over distances as short as a few millimeters from the center of a fuel element to the sidewalls or rim of the fuel element. It is often desired to know or estimate the thermal conductivity and the thermal diffusivity of a material to estimate or predict performance or other properties of the material.

BRIEF SUMMARY

Embodiments disclosed herein include apparatuses for determining at least one of a thermal conductivity and a thermal diffusivity of a material, and related methods. For example, in accordance with one embodiment, a method of determining the thermal conductivity and the thermal diffusivity of a material comprises exposing a specimen comprising a substrate of a material and a metallic film over the substrate to an amplitude modulated pump laser beam comprising electromagnetic radiation having a first wavelength and a first modulation frequency to form a pump spot on the metallic film; exposing the specimen to a probe laser beam comprising electromagnetic radiation having a second wavelength to form a probe spot on the metallic film; measuring a thermal wave phase shift between the pump laser beam and a reflected probe laser beam while scanning the pump spot relative to the probe spot; changing a modulation frequency of the pump laser beam to a second modulation frequency and scanning the pump spot relative to the probe spot while measuring the phase shift between the pump laser beam and the reflected probe laser beam; determining at least one phase profile of the material, the at least one phase profile comprising a relationship between the thermal wave phase shift and a scan distance between the pump laser beam and the reflected probe laser beam at each of the first modulation frequency and the second modulation frequency; and fitting a continuum-based model comprising inputs of at least the thermal conductivity of the substrate material and the thermal diffusivity of the substrate material to the phase profile of the material by minimizing a difference between the continuum-based model and the phase profile by changing the inputs.

In additional embodiments, an apparatus for determining at least one of a thermal conductivity and a thermal diffusivity of a material comprises a pump laser configured to transmit a pump laser beam comprising amplitude modulated electromagnetic radiation having a first wavelength to a specimen comprising a metallic film overlying a substrate of a material; a first lens and a second lens disposed between the pump laser and the material and positioned such that the pump laser beam passes from the first lens to the second lens prior to contacting the metallic film; a stage operably coupled to pump laser and the first lens and configured to move the first lens and the pump laser relative to the second lens; a probe laser configured to transmit a probe laser beam comprising electromagnetic radiation having a second wavelength; a detector operably coupled to a lock in amplifier configured to measure a phase offset between the pump laser beam and a reflected probe laser beam reflected from the metallic film; and a processor operably coupled to the lock in amplifier and configured to determine a thermal conductivity and a thermal diffusivity of the substrate material by fitting a continuum-based model to a measured phase profile by changing inputs into the continuum-based model, the inputs comprising at least the thermal conductivity of the substrate material and the thermal diffusivity of the substrate material.

In further embodiments, a method of determining a thermal conductivity and a thermal diffusivity of a material comprises forming a metallic layer over a substrate of a material; exposing a surface of the metallic layer to a pump laser beam and a probe laser beam to form a respective pump spot and a probe spot on the metallic layer; scanning the pump spot relative to the probe spot while modulating an amplitude of the pump laser beam at a first modulation frequency; measuring a first phase offset between the pump laser beam and a reflected probe laser beam reflected from the surface of the metallic layer while scanning the pump spot; changing a modulation frequency of the pump laser beam to at least a second modulation frequency and scanning the pump spot relative to the probe spot while modulating the amplitude of the pump laser beam; measuring a second phase offset between the pump laser beam and the reflected probe laser beam while scanning the pump spot at the at least a second modulation frequency; and determining a thermal conductivity and a thermal diffusivity of the substrate material based, at least in part, on the first phase offset and the second phase offset by comparing the measured first phase offset and the second phase offset to a continuum-based model and minimizing differences between each of the first phase offset and the second phase offset and the continuum-based model.

DETAILED DESCRIPTION

Figure 1:
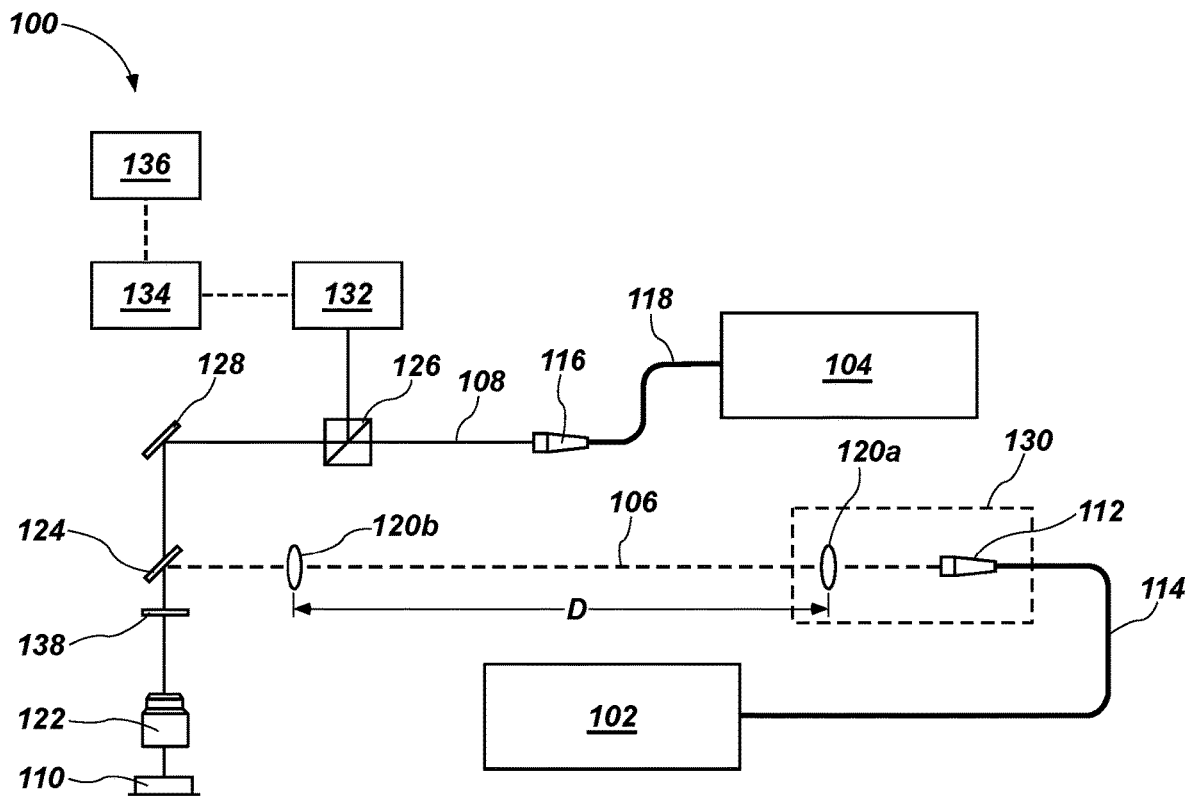
FIG. 1 is a simplified schematic of a system comprising a thermal conductivity microscope for determining a thermal conductivity and a thermal diffusivity of a sample, according to embodiments of the disclosure.

Illustrations presented herein are not meant to be actual views of any particular material, component, or system, but are merely idealized representations that are employed to describe embodiments of the disclosure.

The following description provides specific details, such as material types, dimensions, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional fabrication techniques employed in the industry. In addition, the description provided below does not form a complete process flow, apparatus, system or method for determining a thermal conductivity, a thermal diffusivity, or both of a sample. Only those process acts and structures necessary to understand the embodiments of the disclosure are described in detail below. Additional acts to determine a thermal conductivity, a thermal diffusivity, or both of a sample may be performed by conventional techniques. Also note, any drawings accompanying the present application are for illustrative purposes only, and are thus not drawn to scale. Additionally, elements common between figures may retain the same numerical designation.

According to embodiments described herein, a thermal conductivity and a thermal diffusivity of a material may be determined from a specimen comprising the material with a microscope (e.g., a thermal conductivity microscope). The material specimen may be configured as a metallic film overlying a substrate. The microscope may be configured to measure a phase offset between a pump laser beam and a probe laser beam while scanning a spot of the pump laser beam (i.e., a pump spot) relative to a spot of the probe laser beam (i.e., a probe spot) (i.e., while altering a distance between the pump spot and the probe spot). The pump spot may be scanned relative to the probe spot while operating the pump laser beam at a first modulation frequency. The first modulation frequency of the pump laser beam may be changed to at least a second modulation frequency and the pump spot may be scanned relative to the probe spot while the phase offset is measured. The pump spot may be scanned relative to the probe spot at a plurality of pump laser beam modulation frequencies and the phase offset between the pump laser beam and the reflected probe laser beam may be measured for each modulation frequency during scanning thereof. The pump laser beam may be amplitude modulated. A phase profile, comprising the phase offset (e.g., the thermal wave phase shift) versus the scan distance, may be compared to a theoretical continuum-based model. The continuum-based model may be based on thermodynamics and heat transfer properties of the materials and may include unknowns (e.g., inputs) such as the thermal conductivity of the substrate, the thermal diffusivity of the substrate, a contact resistance between the film and the substrate, and the convolved spot size of the pump spot and the probe spot.

The continuum-based model may be fit to the measured phase profile by changing the inputs (e.g., the thermal conductivity of the substrate, the thermal diffusivity of the substrate, a convolved spot size of the pump spot and the probe spot, and a contact resistance between the metallic film and the substrate (also referred to in the art as a "Kapitza Resistance")). By fitting the continuum-based model to the measured phase profile, the thermal conductivity and the thermal diffusivity of the substrate may be determined.

As used herein, the term "modulation frequency" means and includes a frequency at which a laser (e.g., a pump laser) is turned on and off. Stated another way, modulation frequency means and includes a frequency at which power is supplied to a laser.

Referring to FIG. 1, a system 100 for determining a thermal conductivity and a thermal diffusivity of a material specimen 110 is illustrated. The system 100 may include a pump laser 102 and a probe laser 104 configured to transmit electromagnetic radiation (e.g., a pump laser beam 106 and a probe laser beam 108, respectively) to a surface of the material specimen 110. The pump laser 102 may be operably coupled to an emitter 112 via an optical fiber 114 and the probe laser 104 may be operably coupled to an emitter 116 via another optical fiber 118.

Figure 2:
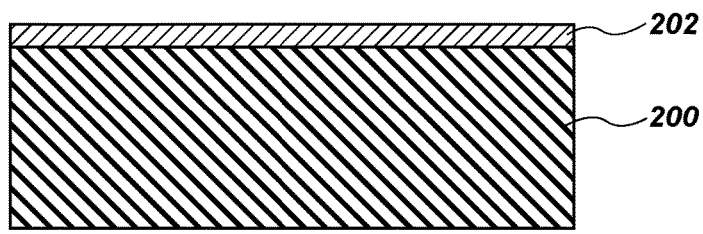
FIG. 2 is a simplified cross-sectional view of a specimen comprising a material to be analyzed, the specimen configured for use with the system of FIG. 1, according to embodiments of the disclosure.

FIG. 2 is a simplified cross-sectional view of the material specimen 110 comprising a material to be analyzed, the material specimen 110 configured for use with the system 100 (FIG. 1). The material specimen 110 may comprise a substrate 200 and a film 202 overlying the substrate 200. The substrate 200 may comprise a material of unknown thermal conductivity, thermal diffusivity, or both, the value or values of which may be determined using system 100. The film 202 may comprise a material exhibiting a desired thermal reflectivity. In some embodiments, the film 202 comprises a metallic film. By way of nonlimiting example, the film 202 may comprise gold, aluminum, titanium, copper, another reflective metal, or combinations thereof.

With reference again to FIG. 1, in some embodiments, the pump laser 102 comprises a continuous wave laser. The pump laser beam 106 may exhibit a power output between about 1 mW and about 50 mW. The pump laser beam 106 may be amplitude modulated. In some embodiments, the power output of the pump laser beam 106 may be modulated between about 1 mW and about 50 mW. The power output of the pump laser beam 106 may be selected such that the pump laser beam 106 does not substantially damage the material specimen 110. In some embodiments, the power output of the pump laser beam 106 is less than about 10 mW at the surface of the material specimen 110.

The pump laser 102 may be configured to generate the pump laser beam 106 at a wavelength that is different than a wavelength of the probe laser beam 108. In some embodiments, the pump laser 102 is configured to generate a pump laser beam 106 having a wavelength of about 660 nm. In some embodiments, the pump laser beam 106 comprises a substantially monochromatic wavelength.

The pump laser beam 106 may pass from the emitter 112 through a pair of confocal lenses comprising a first lens 120a and a second lens 120b. The first lens 120a and the second lens 120b may be configured to focus the pump laser beam 106 and form a pump spot at different locations on the film 202 (FIG. 2) on the surface of the material specimen 110. In addition, the first lens 120a and the second lens 120b may be configured to collimate the electromagnetic radiation (e.g., the light) of the pump laser beam 106. In some embodiments, the first lens 120a and the second lens 120b are substantially similar (i.e., are about the same size, have substantially the same focal length, etc.). A distance, D, between the first lens 120a and the second lens 120b may be equal to a sum of the focal length of the first lens 120a and a focal length of the second lens 120b. In some embodiments, the first lens 120a and the second lens 120b exhibit the same focal length and the distance, D, is equal to about two focal lengths of the first lens 120a. In some embodiments, the distance, D, may be between about 100 mm and about 200 mm, such as about 150 mm.

In some embodiments, the first lens 120a may be configured to move relative to the second lens 120b. In some such embodiments, the first lens 120a and the emitter 112 may be disposed on a movable stage 130. The movable stage 130 may be configured to move in a first direction and a second direction, each of the first direction and the second direction orthogonal to a direction between the first lens 120a and the second lens 120b. In other words, the movable stage 130 may be configured to move in the z-direction (e.g., in the vertical direction in FIG. 1) and in the y-direction (e.g., into and out of the plane of FIG. 1). In some embodiments, the distance, D, may remain the same while the first lens 120a is moved relative to the second lens 120b. Stated another way, the movable stage 130 may be moved without substantially changing a lateral distance, D, between the first lens 120a and the second lens 120b. In other words, a relative distance between the first lens 120a and the second lens 120b in the x-direction (i.e., the horizontal direction in FIG. 1) may remain substantially the same during movement of the movable stage 130.

Movement of the first lens 120a relative to the second lens 120b may change an angle of incidence of the pump laser beam 106 to an objective lens 122. Changing the angle of incidence to the objective lens 122 may change a location of the pump spot on the surface of the material specimen 110. In some embodiments, the probe spot is maintained at substantially a same position at the surface of the material specimen 110 while the pump spot is scanned across the surface of the material specimen 110.

In some embodiments, the system 100 is configured such that movement of the first lens 120a by about 1 mm may move the pump spot on the surface of the material specimen 110 by a distance on the order of microns. Accordingly, an accuracy of the scan distance may be increased with use of the first lens 120a and the second lens 120b in combination.

A spot size of the pump spot on the surface of the material specimen 110 may be between about 1 µm and about 3 µm, such as between about 1.5 µm and about 2.5 µm. In some embodiments, the spot size of the pump spot is between about 1.5 µm and about 2.0 µm. In some embodiments, the spot size is equal to about 1.5 µm or about 2.0 µm. In some embodiments, the spot size of the pump spot and the spot size of the probe spot are substantially negligible relative to dimensions of the material specimen 110.

With continued reference to FIG. 1, the probe laser 104 may comprise a continuous wave laser. The probe laser 104 may be configured to generate a probe laser beam 108 having a different wavelength than the pump laser beam 106. In some embodiments, the probe laser 104 may be configured to generate a probe laser beam 108 having a substantially monochromatic wavelength. In some embodiments, the probe laser beam 108 may have a wavelength that is different from a wavelength of the pump laser beam 106. In some embodiments, the wavelength of the probe laser beam 108 may be selected based on a thermal reflectance of the film 202 (FIG. 2). Stated another way, the wavelength of the probe laser beam 108 may be selected such that the film 202 exhibits a relatively large coefficient of thermal reflectance. By way of nonlimiting example, where the film 202 comprises gold, the wavelength of the probe laser beam 108 may be about 532 nm. In other embodiments, the probe laser beam 108 may have a wavelength of about 488 nm. In yet other embodiments, such as where the film 202 comprises aluminum, the wavelength of the probe laser beam 108 may be selected to be equal to about 800 nm.

The probe laser beam 108 may pass from the emitter 116 through a polarizing beamsplitter (PBS) 126. The polarizing beamsplitter 126 may be configured to facilitate transmission of electromagnetic radiation (e.g., the probe laser beam 108) exhibiting a predetermined polarization while reflecting electromagnetic radiation exhibiting other polarizations. The probe laser beam 108 may pass through the polarizing beamsplitter 126 to an angled mirror 128 where it may be reflected toward the material specimen 110. From the angled mirror 128, the probe laser beam 108 may pass through a dichroic mirror 124, which may be configured to facilitate transmission of electromagnetic radiation having a wavelength of the probe laser beam 108 while reflecting electromagnetic radiation having a wavelength of the pump laser beam 106.

After passing through the dichroic mirror 124, the probe laser beam 108 may pass through a quarter waveplate 138. The quarter waveplate 138 may be configured to change a polarization of the probe laser beam 108, for example, from a linear polarization to a circular polarization. The probe laser beam 108 may pass from the quarter waveplate 138 to the objective lens 122 and from the objective lens 122 to the surface of the material specimen 110. In some embodiments, the probe spot may be maintained at substantially the same position on the surface of the material specimen 110 while the pump spot is scanned over the surface of the material specimen 110 relative to the probe spot.

The probe laser beam 108 may be reflected from the surface of the material specimen 110. The reflected probe laser beam 108 may pass through the quarter waveplate 138 where the polarization of the probe laser beam 108 may be altered again (e.g., from a circular polarization to a polarization rotated 90 degrees from the polarization of the probe laser beam 108 emitted from the emitter 116). The reflected probe laser beam 108 may be transmitted through the dichroic mirror 124 and may reflect from the angled mirror 128 toward the polarizing beamsplitter 126. Since the polarization of the probe laser beam 108 has been altered by the quarter waveplate 138 twice, the reflected probe laser beam 108 may be reflected by the polarizing beamsplitter 126 rather than transmitted therethrough.

The reflected probe laser beam 108 may be received by a detector 132. In some embodiments, a wavelength selective absorption filter may be disposed between the detector 132 and the polarizing beamsplitter 126. The wavelength selective absorption filter may be configured to absorb electromagnetic radiation having a wavelength other than that of the probe laser beam 108 and substantially reduce or eliminate electromagnetic radiation of the pump laser beam 106 from being received by the detector 132.

The detector 132 may comprise a photodiode and may be configured to measure the thermal reflectivity of the material specimen 110. The detector 132 may be operably coupled to a lock in amplifier 134. An output signal (e.g., a voltage) may be transmitted from the detector 132 to the lock in amplifier 134.

The lock in amplifier 134 may be phase locked to the modulation amplitude of the pump laser 102. The lock in amplifier 134 may compare a phase of the pump laser beam 106 to a phase of the reflected probe laser beam 108 and measure the phase shift between the pump laser beam 106 and the reflected probe laser beam 108. As used herein, reference to the "phase shift" of the probe laser beam 108 refers to the relative difference between the phase of the reflected probe laser beam 108 and the phase of the pump laser beam 106. The phase shift may be a negative phase lead (e.g., a positive phase lag). The term "phase shift" may be used interchangeably with "phase offset", "phase lag", or "thermal wave phase offset." As used herein, the term "reflected probe laser beam" refers to a portion of electromagnetic radiation of the probe laser beam 108 that is reflected from the surface of the material specimen 110.

The lock in amplifier 134 may be operably coupled to a processor 136 that may be configured to record the measured phase shift of the reflected probe laser beam 108. The phase shift of the reflected probe laser beam 108 may be continuously measured as the pump spot is moved relative to the probe spot.

According to embodiments described herein, the probe laser beam 108 (FIG. 1) may be used to determine a relative change in temperature on the surface of the material specimen 110 as the pump spot is scanned relative to the probe spot. Changes in temperature on the surface of the material specimen 110 may be caused by local heating of the material specimen 110 from the pump laser beam 106. Since the amplitude (and hence, the power) of the pump laser beam 106 is modulated, the temperature change in the surface of the material specimen 110 may change sinusoidally, corresponding to the amplitude modulation of the pump laser beam 106. A reflected probe laser beam may exhibit a modulation caused by the temperature change in the surface of the material specimen 110 caused by the modulated pump laser beam 106.

The temperature on the surface of the material specimen 110 (FIG. 1) may be correlated to the phase offset between the pump laser beam 106 and the reflected probe laser beam 108. The phase offset may be related to the distance between the pump laser beam 106 and the reflected probe laser beam 108, the thermal properties (e.g., the thermal conductivity, the thermal diffusivity) of the substrate material of material specimen 110, and the contact resistance between the film 202 (FIG. 2) and the substrate 200 (FIG. 2). By way of nonlimiting example, if the substrate 200 of material specimen 110 comprises a relatively high thermal conductivity, the phase offset between the reflected probe laser beam 108 and the pump laser beam 106 may be relatively low compared to embodiments in which the thermal conductivity of the material specimen 110 is relatively low. Without wishing to be bound by any particular theory, it is believed that for materials exhibiting a high thermal conductivity, thermal transfer occurs rapidly, and therefore, a lower phase shift is observed. As another example, as the scan distance increases, the phase offset may increase since it may take a longer time to observe thermal transfer through the material specimen 110 between the probe spot and the pump spot.

Accordingly, the phase offset may be correlated to thermal transport from the pump laser beam 106 to the film 202 (FIG. 2), thermal transport through the film 202 in the lateral direction, thermal transport through the film 202 in the vertical direction (i.e., across a thickness thereof), the contact resistance between the film 202 and the substrate 200, and thermal transport through the substrate 200. Stated another way, the phase offset may be related to the thermal conductivity of the film 202, the thermal conductivity of the substrate 200, the thermal diffusivity of the film 202, the thermal diffusivity of the substrate 200, and the contact resistance between the film 202 and the substrate 200.

Figure 3A:
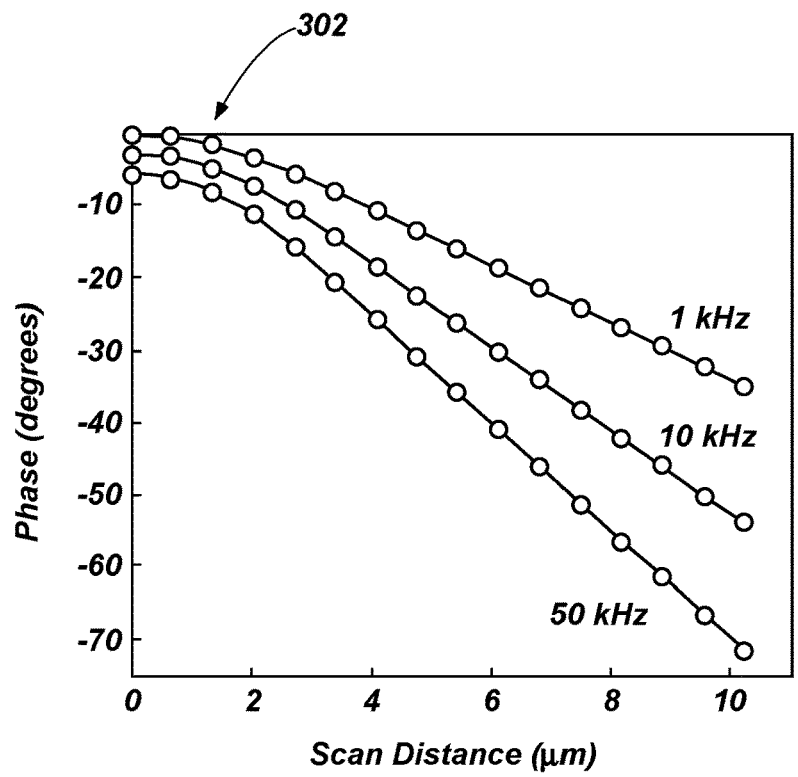
FIG. 3A is a phase profile graph of a material, according to embodiments of the disclosure.

As a distance between the pump laser beam 106 and the probe laser beam 108 on the surface of the material specimen 110 is increased, the phase shift may increase. FIG. 3A is a graph of the phase shift of the reflected probe laser beam 108 (FIG. 1) relative to the pump laser beam 106 (FIG. 1) versus the scan distance at several modulation frequencies of the pump laser beam 106. As used herein, the term "scan distance" means and includes a distance between the pump spot and the probe spot on the surface of the material specimen 110 (FIG. 1). As used herein, the term "phase profile" refers to the correlation between the phase offset of the reflected probe laser beam 108 relative to the pump laser beam 106 and the scan distance at one or more frequencies of the pump laser beam 106, as represented graphically in FIG. 3A.

The scan distance may be between about 0 μm (i.e., the probe spot may directly overlie and overlap the pump spot) and about 20 μm. Stated another way, the distance between the pump spot and the probe spot may be between about 0 μm and about 20 μm. As described above, the pump spot may be scanned on the film 202 (FIG. 2) while the probe spot is maintained at substantially a same position of the surface of the film 202.

In some embodiments, the thermal transfer and thermal properties of the material specimen 110 may be modeled using a theoretical continuum-based model comprising thermodynamic equations and heat transfer equations incorporating unknown parameters such as the thermal diffusivity of the substrate 200 (FIG. 2), the thermal conductivity of the substrate 200, the contact resistance between the substrate 200 and the film 202 (FIG. 2), and the convolved spot size of the probe laser beam 108 and the pump laser beam 106. The temperature profile (and, therefore, the phase offset) of the material specimen 110 may also depend on other factors including, for example, the thermal conductivity and the thermal diffusivity of the film 202, which may be known prior to measuring the thermal properties of the material specimen 110. By way of nonlimiting example, a film 202 of a known composition (and exhibiting a known thermal conductivity and thermal diffusivity) may be coated onto the substrate 200 prior to measuring the phase offset.

The continuum-based model including thermodynamic equations and heat transfer equations may be substantially similar to those described in "Harmonic heat flow in isotropic layered systems and its use for thin film thermal conductivity measurements" by Reichling et al., Journal of Applied Physics, 75, pp. 1914-1922 (1994), the entire disclosure of which is hereby incorporated herein in its entirety by this reference. By way of nonlimiting example, the temperature rise in the substrate 200 (FIG. 2) and the film 202 (FIG. 2) may be correlated to the thermal diffusivity and thermal conductivity of the substrate 200 and film 202, respectively, and the energy input into the respective regions according to Equation 1 and Equation 2 below:

$$\nabla^2 T_f - \frac{1}{k_f}\frac{\partial T_f}{\partial t} = -\frac{Q_f}{K_f}, \quad \text{Eq (1)}$$

$$\nabla^2 T_s - \frac{1}{k_s}\frac{\partial T_s}{\partial t} = -\frac{Q_s}{K_s}, \quad \text{Eq (2)}$$

wherein $k_f$ is the thermal diffusivity of the film 202, $K_f$ is the thermal conductivity of the film 202, $k_s$ is the thermal diffusivity of the substrate 200, $K_s$ is the thermal conductivity of the substrate 200, and $Q_f$ and $Q_s$ are the energy input into the film 202 and the substrate 200, respectively.

At the interface between the substrate 200 (FIG. 2) and the film 202 (FIG. 2), a finite temperature step may correspond to a contact resistance Rth between the substrate 200 and the film 202, according to Equation 3 below. Similarly, at the interface, the change in temperature of the substrate 200 in the direction of the thickness of the material specimen 110 (FIG. 2) (in the z-direction) may be equal to a change in temperature of the substrate 200 in the z-direction, according to Equation 4 below.

$$-K_f \frac{\partial T_f}{\partial z} = \frac{1}{R_{th}}(T_s - T_f), \quad \text{Eq (3)}$$

$$-K_f \frac{\partial T_f}{\partial z} = K_s \frac{\partial T_s}{\partial z} \text{ (at interface)}, \quad \text{Eq (4)}$$

wherein $T_s$ and $T_f$ are the temperature of the substrate and the film, respectively.

The energy input into the film 202 (FIG. 2) may be related to the total power of the pump laser beam 106 (FIG. 1), as indicated in Equation 5 below. The energy input into the substrate 200 (FIG. 2) may be represented as Equation 6 below.

$$Q_f = (1-R_f)\frac{2\alpha_f P}{\pi a^2}e^{-2(\frac{r}{a})^2}e^{-\alpha_f z} * \frac{1}{2}\left(1+\frac{1}{2}(e^{i\omega t}+e^{-i\omega t})\right), \quad \text{Eq (5)}$$

$$Q_s = (1-R_f)(1-R_s)\frac{2\alpha_s P}{\pi a^2}e^{-2(\frac{r}{a})^2}e^{-(x-L_f)\alpha_s}e -$$
$$\alpha_f l_f * \frac{1}{2}\left(1+\frac{1}{2}(e^{i\omega t}+e^{-i\omega t})\right), \quad \text{Eq (6)}$$

wherein P is the power of the pump laser beam 106, $R_f$ and $R_s$ are the optical reflectivity of the film 202 and the substrate 200, respectively, $\alpha_f$ and $\alpha_s$ are the optical absorption coefficients of the film 202 and the substrate 200, respectively, a is the radius of the pump laser beam 106, r is the radial distance from a center of the pump laser beam 106 to a center of the probe laser beam 108, z is the depth below the surface of the film 202, ω is the angular frequency of the pump laser beam 106, and $L_f$ is the thickness of the film 202.

Because the probe laser beam 108 exhibits cylindrical symmetry, the differential equations may be solved using Hankel transform techniques, as known in the art and as described in previously referenced Reichling et al., Journal of Applied Physics, 75, pp. 1914-1922 (1994).

In some embodiments, the thermal properties of the substrate 200 (FIG. 2) and film 202 (FIG. 2) may be approximated by assuming that the film 202 is thermally conductive, the substrate 200 is thermally insulative, and treating the pump beam 106 as a far field source. In some such embodiments, the slope of the phase profile (q) may be approximated according to Equation 7 below:

$$q^2 = \frac{i w}{D_f} + \frac{q_0}{2}\left[1-\sqrt{1-\frac{4iw}{D_s q_0^2}}\left(1-\frac{D_s}{D_f}\right)\right], \quad \text{Eq (7)}$$

wherein q is the slope of the phase profile, $q_0$ is equal to $k_s/hk_f$, where $k_s$ is the thermal conductivity of the substrate, $k_f$ is the thermal conductivity of the film, h is the film thickness, $D_s$ is the diffusivity of the substrate, and $D_f$ is the diffusivity of the film.

Accordingly, the thermal conductivity and thermal diffusivity of the substrate 200, the contact resistance between the substrate 200 and the film 202, and the convolved spot size may be correlated to the phase profile as described above with reference to Equation 1 through Equation 7. Stated another way, the phase profile may be a function of each of the thermal conductivity and the thermal diffusivity of the substrate 200, the contact resistance between the substrate 200 and the film 202, and the convolved spot size.

In some embodiments, an accuracy of the determined thermal conductivity and the thermal diffusivity of the substrate 200 may be increased by selecting modulation frequencies at which the phase profile exhibits a sensitivity to one or more of the unknown parameters (e.g., to one or more of the thermal conductivity of the substrate 200, the thermal diffusivity of the substrate 200, the contact resistance between the substrate 200 and the film 202, or the convolved spot size of the pump spot and the probe spot) and measuring the phase offset at such modulation frequencies. By way of nonlimiting example, the modulation frequency may be selected to be about 100 kHz and the radial distance from the center of the probe laser beam 108 may be selected to be about 0 (i.e., r=0) to facilitate extraction of the contact resistance between the substrate 200 and the film 202.

With continued reference to FIG. 3A, at relatively small scan distances, (e.g., less than about 4 μm, such as between about 0 μm and about 2 μm), the phase offset exhibits an increased sensitivity to the spot size, as indicated in region marked by arrow 302. At scan distances greater than about 4 μm, the phase offset between the pump laser beam 106 and the probe laser beam 108 becomes linear with scan distance. At the larger scan distances (e.g., at scan distances greater than, for example, about 4 μm) the phase offset between the pump laser beam 106 and the probe laser beam 108 are related to the thermal conductivity and the thermal diffusivity of the material specimen 110 (e.g., of each of the substrate 200 (FIG. 2) and the film 202 (FIG. 2)). Stated another way, the phase shift is substantially related to the thermal conductivity and the thermal diffusivity of the substrate 200 and the film 202 at scan distances greater than, for example, 4 μm. Accordingly, the scan distance may be ranged from about zero up to a value large enough that the phase shift exhibits a desired sensitivity to the thermal conductivity and thermal diffusivity of the substrate 200.

Figure 3B:
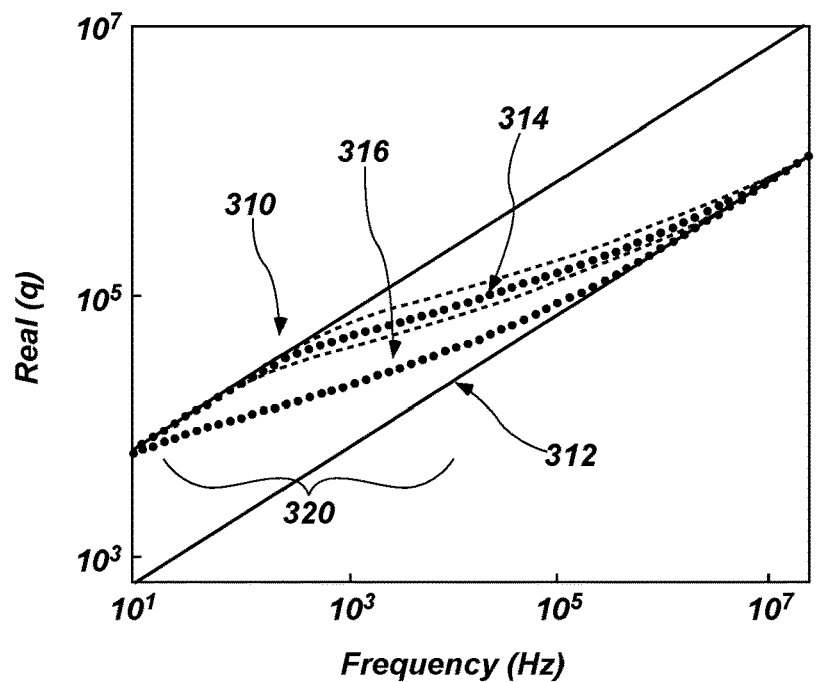
FIG. 3B is a graph illustrating a slope of the phase profile versus modulation frequency of the pump laser beam, according to embodiments of the disclosure.

FIG. 3B is a graph illustrating a slope of the phase profile (q) (i.e., the slope of FIG. 3A) versus the modulation frequency of the pump laser beam 106. The slope of the phase profile may be equal to an amount of change of the phase offset per change in scan distance (i.e., degrees of phase offset per micron change in scan distance). Line 310 corresponds to the slope of the phase profile for a system including only the substrate 200 (FIG. 2). Line 312 corresponds to the slope of the phase profile for a system including only the film 202 (FIG. 2). The slope of the phase profile is illustrated for a sample wherein a thickness of the film 202 (FIG. 2) is equal to about 60 nm (as indicated by arrow 314) and another sample having a film 202 (line 316) with a thickness of about 300 nm. The relatively smaller dots above and below line 314 represent the slope of the phase profile of a substrate having a 50% lower and a 50% greater thermal conductivity, respectively, than the substrate of line 314.

In some embodiments, the slope of the phase profile at low modulation frequencies may be related to the thermal diffusivity of the substrate 200 whereas the slope of the phase profile at high modulation frequencies may be related to the thermal diffusivity of the film 202. At intermediate modulation frequencies, such as in a transition region 320, the slope of the phase profile may be dependent on the thermal conductivity and the thermal diffusivity of each of the substrate 200 and the film 202. The transition region 320 of the sample illustrated in FIG. 3B is at a modulation frequency between about 10 Hz and about $10^4$ Hz.

Accordingly, the thermal diffusivity and the thermal conductivity of the material of substrate 200 may be determined by measuring the phase profile over a range of modulation frequencies spanning from low modulation frequencies (i.e., at modulation frequencies where the slope of the phase profile is dependent on the thermal conductivity of the substrate 200) to intermediate modulation frequencies (i.e., at modulation frequencies where the slope of the phase profile is dependent on the thermal conductivity and the thermal diffusivity of each of the substrate 200 and the film 202. Stated another way, in some embodiments, the thermal diffusivity and the thermal conductivity of the substrate 200 may be determined by measuring the phase profiles at a plurality of modulation frequencies spanning the transition region 320 (e.g., from low modulation frequencies to intermediate modulation frequencies). In some embodiments, the transition region 320 may correspond to lower modulation frequencies as a thickness of the film 202 increases.

In some embodiments, the modulation frequency range at which the phase offset (and, hence, the phase profile) is measured may be determined based on one or more factors including, for example, noise of the system (e.g., low frequency laser noise) and the slope of the phase profile at the scanned modulation frequency. As illustrated in FIG. 3B, the slope of the phase profile may increase with an increase in modulation frequency. Accordingly, at lower modulation frequencies, the lower slope may increase an error of determining the thermal conductivity or the thermal diffusivity of the substrate 200 (FIG. 2). In some embodiments, above the upper modulation frequency, the phase profile may be attenuated by a relatively low signal strength and a relatively short diffusion length. By way of nonlimiting example, the diffusion length of the material specimen 110 may be a function of material properties of the material specimen 110 and may also be a function of the modulation frequency. In some embodiments, the modulation frequency is selected such that the diffusion length is greater than the spot size. Selecting the modulation frequency such that the diffusion length is greater than the spot size may increase an accuracy of the thermal diffusivity and thermal conductivity of the material specimen 110 determined by the method described herein. The upper modulation frequency may be selected such that the signal amplitude measured by the probe laser beam 108 is greater than the noise of the system 100.

In some embodiments, the thickness of the film 202 may be selected to optimize a sensitivity of the phase profile to the thermal properties of the substrate 200. In some embodiments, the thickness of the film 202 may be selected such that the film 202 exhibits a strong optical absorption and exhibits a high sensitivity to the thermal conductivity of the substrate 200 at higher frequencies.

Figure 4:
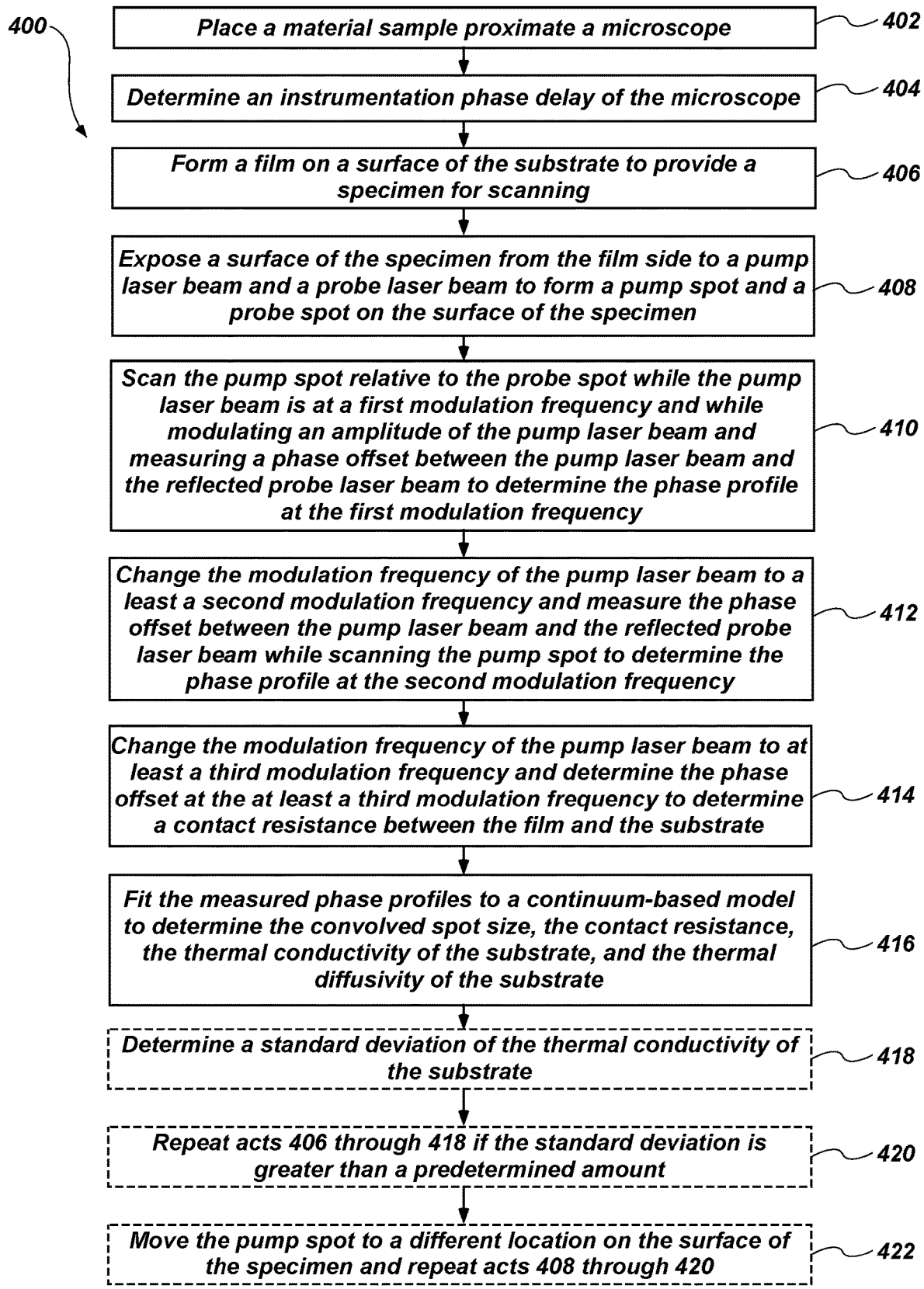
FIG. 4 is a simplified flow diagram of a method of determining a thermal conductivity and a thermal diffusivity of a sample, according to embodiments of the disclosure.

FIG. 4 is a method 400 of determining a thermal conductivity and a thermal diffusivity of a substrate. The method 400 includes act 402 including placing a material sample comprising a substrate proximate a microscope; act 404 including determining an instrumentation phase delay of the microscope; act 406 including forming a film on a surface of the substrate to provide a specimen for scanning; act 408 exposing a surface of the specimen from the film side to a pump laser beam and a probe laser beam to form a pump spot and a probe spot on the surface of the specimen; act 410 including scanning the pump spot relative to the probe spot while the pump laser beam is at a first modulation frequency and while modulating an amplitude of the pump laser beam and measuring a phase offset between the pump laser beam and the probe laser beam to determine the phase profile at the first modulation frequency; act 412 including changing the modulation frequency of the pump laser beam to at least a second modulation frequency and measuring the phase offset between the pump laser beam and the probe laser beam while scanning the pump spot to determine the phase profile at the second modulation frequency; act 414 including changing the modulation frequency of the pump laser beam to at least a third modulation frequency and determining the phase profile at the at least a third modulation frequency to determine a contact resistance between the film and the substrate; act 416 including fitting the measured phase profiles to a mathematical model to determine the convolved spot size, the contact resistance, the thermal conductivity of the substrate, and thermal diffusivity of the substrate; act 418 including determining a standard deviation of the thermal conductivity of the substrate; act 420 including repeating acts 406 through 416 if the standard deviation is greater than a predetermined amount; and act 422 including moving the pump spot to a different location on the surface of the specimen and repeating acts 408 through 420.

Act 402 includes placing a material sample comprising a substrate of a material of unknown thermal conductivity and thermal diffusivity proximate a microscope (e.g., system 100 (FIG. 1)). In some embodiments, the substrate may comprise a nuclear fuel pellet that may be disposed in a nuclear reactor including a shielded nuclear radiation containment chamber (also referred to in the art as a "hot cell"). In some embodiments, the microscope may be located within the hot cell.

Act 404 includes determining an instrumentation phase delay between the pump laser beam and the probe laser beam due to instrumentation of the microscope. In some embodiments, the pump laser beam may be directed directly into a detector (e.g., detector 132 (FIG. 1)) and the lock in phase may be recorded. In some embodiments, the modulation frequency of the pump laser beam may be selected to be at modulation frequencies at which the phase offset is sensitive to the contact resistance between the substrate and the film, as will be described herein. In some embodiments, the pump laser beam modulation frequency may be equal to about 100 kHz when determining the phase delay of the microscope.

Act 406 includes forming a film (e.g., film 202 (FIG. 2)) on a surface of the substrate to provide a specimen for scanning. In some embodiments, the film may be formed on the substrate by sputter coating the film on the substrate while the substrate is in the hot cell. In some such embodiments, the hot cell may include a sputter deposition chamber. In yet other embodiments, the film may be formed on the substrate by one or more film deposition techniques, such as one or more of chemical vapor deposition (CVD), atomic layer deposition (ALD), physical vapor deposition (PVD), or other deposition method for forming a layer of material over a substrate. By way of nonlimiting example, the film may be formed to a thickness between about 10 nm and about 500 nm, although the disclosure is not so limited and the film may be formed to other thicknesses.

Act 408 includes exposing a surface of the specimen (e.g., the film) from the film side to the pump laser beam and a probe laser beam to form a pump spot and a probe spot on the surface of the specimen (e.g., a surface of the film). The pump spot and the probe spot may be substantially similar to those described above with reference to FIG. 1.

Act 410 includes scanning the pump spot relative to the probe spot while the pump laser beam is at a first modulation frequency and while modulating an amplitude of the pump laser beam. Act 410 may further include measuring a phase offset between the pump laser beam and the reflected probe laser beam while scanning the pump spot to determine the phase profile at the first modulation frequency. In some embodiments, the phase offset measured at a scan distance of zero may be subtracted from the phase offset in the phase profile. In some embodiments, the first modulation frequency may be selected to be a modulation frequency within the transition region 320 (FIG. 3B), such as a modulation frequency between about 1 kHz and about 100 kHz, although the disclosure is not so limited. In some embodiments, the pump laser beam may be amplitude modulated as described above with reference to the pump laser beam 106 (FIG. 1). Although, act 410 has been described as including scanning the pump spot relative to the probe spot, in other embodiments, the probe spot may be scanned relative to a substantially stationary pump spot.

Act 412 includes changing the modulation frequency of the pump laser beam to at least a second modulation frequency and measuring the phase offset between the pump laser beam and the reflected probe laser beam while scanning the pump spot to determine the phase profile at the second modulation frequency. In some embodiments, the phase offset measured at a scan distance of zero may be subtracted from the phase offset in the phase profile. The at least a second modulation frequency may be selected to be a modulation frequency within the transition region 320 (FIG. 3B). In some embodiments, the at least a second modulation frequency may comprise between at least two different modulation frequencies and at least eight different modulation frequencies. Stated another way, the phase offset between the pump laser beam and the probe laser beam may be measured for between at least about two different modulation frequencies and about at least eight different modulation frequencies to determine the phase profile at each of the selected modulation frequencies. However, the disclosure is not so limited and the phase offset may be measured for a different number of modulation frequencies. As described above, measuring the phase offset at a plurality of modulation frequencies may increase a sensitivity of the phase offset to one or more unknown properties (e.g., thermal conductivity of the substrate, thermal diffusivity of the substrate, or convolved spot size).

Act 414 includes changing the modulation frequency of the pump laser beam to at least a third modulation frequency and determining a contact resistance between the film and the substrate of the specimen. The phase offset between the pump laser beam and the reflected probe laser beam may be sensitive to the contact resistance at high modulation frequencies and at low scan distances. Accordingly, act 414 may include measuring the phase offset at low scan distances (e.g., such as where the pump spot and the probe spot substantially overlay (i.e., a scan distance of about zero)) and at a modulation frequency higher than the modulation frequencies described above with reference to acts 408 through 412. Without wishing to be bound by any particular theory, it is believed that at high modulation frequencies and at a scan distance of about zero, the phase offset is most closely related to thermal effusivity and the measurement of effusivity depends on the boundary condition between the film and the substrate. In addition, the phase offset at high modulation frequencies and small scan distances is dependent on thermal transport in the depth direction of the sample, whereas thermal transport at high modulation frequencies and higher scan distances is also dependent on thermal diffusivity and thermal conductivity in the lateral direction. Accordingly, by selecting the at least a third modulation frequency and the scan distance at predetermined values, the contact resistance may be determined with accuracy.

In some embodiments, the at least a third modulation frequency may be selected to be a modulation frequency at an upper range of the transition region 320 (FIG. 3B). In some embodiments, the at least a third modulation frequency may be selected to be equal to a modulation frequency at which the instrumentation phase delay is measured in act 404. Although act 414 has been described as being performed after act 404, the disclosure is not so limited. In other embodiments, act 414 may be performed after act 404 or substantially concurrently with act 404. In some embodiments, the phase offset at a scan distance of about zero may not be subtracted from the phase profile. Without wishing to be bound by any particular theory, it is believed that the phase offset at a scan distance of about zero at the higher modulation frequency is a function of the contact resistance and may facilitate extraction of the contact resistance.

Act 416 includes fitting the measured phase profiles to the continuum-based model to determine the convolved spot size, the thermal conductivity of the substrate, and thermal diffusivity of the substrate. In some embodiments, the parameters (e.g., the thermal conductivity of the substrate, the thermal diffusivity of the substrate, the convolved spot size, and the contact resistance) of the continuum-based model may be adjusted to minimize an error between the continuum-based model and the measured phase profile. In some embodiments, the error between the model and the measured phase profiles may be minimized by fitting the continuum-based model to the measured phase profile with the Nelder-Mead direct search method. In other embodiments, the error between the continuum-based model and the measured phase profiles may be minimized by changing the unknown parameters and minimizing the difference between the sum of the squares of the difference between the model and the measured phase profiles, as known in the art of numerical analysis. In other embodiments, the unknown parameters may be determined by multivariate analysis (MVA) as may be known in the art of numerical analysis.

In some embodiments, an accuracy of the determined thermal conductivity and thermal diffusivity may be determined, as will be described with reference to acts 418 and 420. By way of nonlimiting example, optional act 418 includes determining the standard deviation of the thermal conductivity of the substrate. In some embodiments, the standard deviation is measured by performing a linear regression analysis of the measured phase profiles (i.e., the phase profiles at each of the modulation frequencies), as may be known in the art of numerical analysis. If the standard deviation is less than a predetermined amount (e.g., less than about five percent (5%)), the method 400 may be complete.

In other embodiments, such as where the standard deviation of the thermal conductivity is greater than a predetermined amount (e.g., greater than about five percent (5%)), the method 400 includes recoating the material sample with an optimal film thickness, which may be determined using the determined value of the thermal diffusivity of the material of the substrate. By way of nonlimiting example, the determined value of the thermal diffusivity may be input into the continuum-based model to determine the optimal thickness of the film. In some embodiments, an optimal film thickness may be estimated by performing a sensitivity analysis on film thickness as described in "Local measurement of thermal conductivity and diffusivity" by Hurley et al., Review of Scientific Instruments 86, 123901 (2015), the entire disclosure of which is hereby incorporated herein in its entirety by this reference.

In some embodiments, a standard deviation greater than the predetermined amount may correspond to the use of an improper film 202 (FIG. 2) thickness (e.g., a film thickness wherein the thermal conductivity and thermal diffusivity measurements are not as sensitive to phase offset and modulation frequency as a more optimal film thickness). In some such embodiments, acts 406 through 418 may be repeated with a new film thickness. In other words, a film 202 having a different thickness may be formed on the substrate 200 (or another substrate, such as another fuel element in a nuclear reactor) and the thermal conductivity and thermal diffusivity may be determined as described with reference to acts 406 through 418.

In some embodiments, the pump spot may be moved to a different location on the surface of the specimen and acts 408 through 420 may be repeated to determine the thermal conductivity and the thermal diffusivity of the substrate at a different location of the specimen. In some embodiments, moving the pump spot to a different location of the surface of the specimen may facilitate determining the thermal conductivity and thermal diffusivity of specimens exhibiting an anisotropic thermal conductivity (e.g., different thermal conductivity values in different directions of the specimen).

Accordingly, by selecting the modulation frequency range and the scan distances at which the phase offset is measured, the thermal conductivity and the thermal diffusivity of the material may be determined with substantially accuracy. Compared to prior art methods, according to the methods described herein, the thermal conductivity and the thermal diffusivity of a material may be determined without prior knowledge of the spot size of the pump spot or the probe spot. In addition, the methods described herein include determining the thermal conductivity substantially simultaneously with determining the thermal diffusivity of the material.

The thermal conductivity and thermal diffusivity may be determined for material samples having a smaller size compared to other methods of determining thermal properties. By way of nonlimiting example, nuclear fuels may exhibit cracks and other heterogeneities with length scales that span microns to millimeters in length. The methods described herein may be used to determine thermal conductivity and thermal diffusivity of material samples having a dimension (e.g., length, width, etc.) greater than about ten microns, or a dimension less than about one millimeter.

In some embodiments, the configuration of the first lens 120a (FIG. 1) and the second lens 120b (FIG. 1) may facilitate scanning the pump spot relative to the probe spot with substantial accuracy. Since the pump beam may be scanned with accuracy across the surface of a sample, the thermal conductivity may be determined in one or more directions. B y way of nonlimiting example, some materials may exhibit different thermal conductivity values in different directions (i.e., may exhibit anisotropic thermal conductivity). In some such embodiments, accurately scanning the pump beam relative to the probe beam with the system 100 (FIG. 1) described herein, may facilitate determining the thermal conductivity values of anisotropic materials. In addition, the thermal conductivity of samples having a small size (e.g., on the order of microns) may be determined using the methods described herein.

While embodiments of the disclosure may be susceptible to various modifications and alternative forms, specific embodiments have been shown by way of example in the drawings and have been described in detail herein. However, it should be understood that the disclosure is not limited to the particular forms disclosed. Rather, the disclosure encompasses all modifications, variations, combinations, and alternatives falling within the scope of the disclosure as defined by the following appended claims and their legal equivalents.

What is claimed is:

1. A method of determining a thermal conductivity and a thermal diffusivity of a material, the method comprising:
    exposing a specimen comprising a substrate of a material and a metallic film over the substrate to an amplitude modulated pump laser beam comprising electromagnetic radiation having a first wavelength and a first modulation frequency to form a pump spot on the metallic film;
    exposing the specimen to a probe laser beam comprising electromagnetic radiation having a second wavelength to form a probe spot on the metallic film;
    measuring a thermal wave phase shift between the pump laser beam and a reflected probe laser beam while scanning the pump spot relative to the probe spot;
    changing a modulation frequency of the pump laser beam to a second modulation frequency and scanning the pump spot relative to the probe spot while measuring the thermal wave phase shift between the pump laser beam and the reflected probe laser beam;
    determining at least one phase profile of the material, the at least one phase profile comprising a relationship between the thermal wave phase shift and a scan distance between the pump laser beam and the reflected probe laser beam at each of the first modulation frequency and the second modulation frequency;
    measuring a phase offset between the pump laser beam and the probe laser beam at the first modulation frequency and the second modulation frequency after moving the probe spot; and
    determining a thermal conductivity and a thermal diffusivity of the substrate based, at least in part, on the at least one phase profile of the material.

2. The method of claim 1, further comprising scanning the pump spot relative to the probe spot at each of at least three different frequencies of the pump laser beam.

3. The method of claim 1, further comprising selecting the first modulation frequency and the second modulation frequency to be between about 1 kHz and about 100 kHz.

4. The method of claim 1, wherein scanning the pump spot relative to the probe spot comprises moving the pump spot while maintaining a position of the probe spot.

5. The method of claim 1, wherein exposing the specimen to an amplitude modulated pump laser beam comprises transmitting the pump laser beam from an emitter through a confocal lens pair, the confocal lens pair comprising a first lens separated from a second lens by a distance equal to about a sum of a focal length of the first lens and the second lens.

6. The method of claim 5, wherein scanning the pump spot relative to the probe spot comprises disposing the emitter and the first lens on a movable stage configured to move in a first direction orthogonal to a direction between the first lens and the second lens and a second direction orthogonal to the direction between the first lens and the second lens.

7. The method of claim 1, wherein scanning the pump spot comprises transmitting the pump laser beam to an objective lens and changing an angle of incidence of the pump laser beam to change a position of the pump spot on the metallic film.

8. The method of claim 1, further comprising selecting the substrate material to comprise a nuclear fuel and selecting the metallic film to comprise one or more of gold, aluminum, titanium, or copper.

9. The method of claim 1, wherein scanning the pump spot relative to the probe spot comprises changing a distance between the pump spot and the probe spot on the metallic film from between about 0 μm to about 20 μm.

10. The method of claim 1, wherein measuring a phase offset between the pump laser beam and the probe laser beam further comprises determining the phase offset of the pump laser beam due to instrumentation.

11. The method of claim 10, further comprising determining a phase offset between the pump laser beam and the reflected probe laser beam while the pump laser beam is at a third modulation frequency greater than the first modulation frequency and the second modulation frequency.

12. The method of claim 11, further comprising determining a contact resistance between the substrate and the metallic film based, at least in part, on the phase offset between the pump laser beam and the reflected probe laser beam at the third modulation frequency.

13. The method of claim 1, further comprising forming the metallic film on the substrate by sputter deposition.

14. The method of claim 13, wherein forming the metallic film on the substrate by sputter deposition comprises forming the metallic film on the substrate while the substrate is in a hot cell.

15. The method of claim 1, further comprising determining a convolved spot size of the probe laser beam and the pump laser beam.

16. The method of claim 1, further comprising moving the probe spot on a surface of the metallic film after determining the thermal conductivity and the thermal diffusivity of the substrate.

17. The method of claim 1, further comprising determining a standard deviation of the determined thermal conductivity and the determined thermal diffusivity.

18. An apparatus for determining at least one of a thermal conductivity and a thermal diffusivity of a material, the apparatus comprising:
    a pump laser configured to transmit a pump laser beam comprising amplitude modulated electromagnetic radiation having a first wavelength to a specimen comprising a metallic film overlying a substrate of a material;
    a first lens and a second lens disposed between the pump laser and the material and positioned such that the pump laser beam passes from the first lens to the second lens prior to contacting the metallic film;
    a stage operably coupled to the pump laser and the first lens and configured to move the first lens and the pump laser relative to the second lens;
    a probe laser configured to transmit a probe laser beam comprising electromagnetic radiation having a second wavelength;
    a detector operably coupled to a lock in amplifier configured to measure a phase offset between the pump laser beam and a reflected probe laser beam reflected from the metallic film; and
    a processor operably coupled to the lock in amplifier and configured to determine a thermal conductivity and a thermal diffusivity of the substrate material based, at least in part, on at least one phase profile of the substrate material.

19. The apparatus of claim 18, wherein a distance between the first lens and the second lens is equal to about a sum of a focal length of the first lens and the second lens.

20. The apparatus of claim 18, further comprising a movable stage configured to move in a first direction and a second direction, each of the first direction and the second direction orthogonal to a direction between the first lens and the second lens.

21. The apparatus of claim 18, further comprising a polarizing beam splitter between the probe laser and a sample.

22. The apparatus of claim 18, further comprising a quarter waveplate between the pump laser and the substrate and between the probe laser and the substrate material.

23. A method of determining a thermal conductivity and a thermal diffusivity of a material, the method comprising:

exposing a specimen comprising a substrate of a material and a metallic film over the substrate to an amplitude modulated pump laser beam comprising electromagnetic radiation having a first wavelength and a first modulation frequency to form a pump spot on the metallic film;

exposing the specimen to a probe laser beam comprising electromagnetic radiation having a second wavelength to form a probe spot on the metallic film;

measuring a thermal wave phase shift between the pump laser beam and a reflected probe laser beam while scanning the pump spot relative to the probe spot;

changing a modulation frequency of the pump laser beam to a second modulation frequency and scanning the pump spot relative to the probe spot while measuring the thermal wave phase shift between the pump laser beam and the reflected probe laser beam;

determining at least one phase profile of the material, the at least one phase profile comprising a relationship between the thermal wave phase shift and a scan distance between the pump laser beam and the reflected probe laser beam at each of the first modulation frequency and the second modulation frequency;

determining a thermal conductivity and a thermal diffusivity of the substrate based, at least in part, on the at least one phase profile of the material; and moving the probe spot on a surface of the metallic film after estimating the thermal conductivity and the thermal diffusivity of the substrate.

* * * * *